United States Patent [19]

Liao et al.

[11] Patent Number: 5,645,983
[45] Date of Patent: Jul. 8, 1997

[54] CORE ANTIGEN PROTEIN OF HEPATITIS C VIRUS, AND DIAGNOSTIC METHOD AND KIT USING THE SAME

[75] Inventors: Jaw-Ching Liao; Cheng-Nan Wang, both of Taipei, Taiwan

[73] Assignee: BioNova Corporation, San Francisco, Calif.

[21] Appl. No.: 143,578

[22] Filed: Oct. 26, 1993

Related U.S. Application Data

[62] Division of Ser. No. 963,483, Oct. 16, 1992, abandoned.
[51] Int. Cl.$^6$ .......................... C12Q 1/70; G01N 33/576; C07K 16/08
[52] U.S. Cl. .......................... 435/5; 436/518; 436/548; 436/820; 530/388.3; 530/389.4
[58] Field of Search .................. 435/5; 436/518, 436/548, 820; 530/388.3, 389.4; 424/89

[56] References Cited

U.S. PATENT DOCUMENTS

| | | | |
|---|---|---|---|
| 5,106,726 | 4/1992 | Wang | 435/5 |
| 5,350,671 | 9/1994 | Houghton et al. | 435/5 |

FOREIGN PATENT DOCUMENTS

| | | |
|---|---|---|
| 0318216 | 5/1989 | European Pat. Off. . |
| 0388232 | 9/1990 | European Pat. Off. . |
| 450931A1 | 10/1991 | European Pat. Off. . |
| WO91/15516 | 10/1991 | WIPO . |
| WO92/11370 | 7/1992 | WIPO . |

OTHER PUBLICATIONS

Muralso et al., A Structural Protein of Hepatitis C Virus Expressed in E. coli Facilitates Accurate Detection of Hepatitis C Virus, Biochemical and Biophysical Research Communications 172(2):511–516, 1990.
Harada et al., Expression of Processed Core Protein of Hepatitis C Virus in Mammalian Cells, Journal of Virology 65(6):3015–3021, 1991.
Clemens, J. M. et al., "IgM Antibody Response in Acute Hepatitis C Viral Infection."*Blood* 79:No. 1, 169–72, 1992.
Chau, K.H. et al., "IgM–antibody response to hepatitis C virus antigens in acute and chronic post–transfusion non–A, non–B hepatitis," *J. of Virological Methods* 35:343–52, 1991.
Sallberg, M. et al., "Immune response to a single peptide containing an immunodominant region of hepatitis C virus core protein: the isotypes and the recognition site," *Immunology Letters* 33:27–34, 1992.

Clark, B. R. et al., "Enzyme–Linked Immunosorbent Assay (Elisa): Theoretical and Practical Aspects," *Enzyme Immunoassay*, pp. 167–179, 1980.
Chen et al., "The Taiwanese Hepatitis C Virus Genome: Sequence Determination and Mapping the 5' Termini of Viral Genomic and Antigenomic RNA," *Virology* 188:102–113, 1992.
Inchauspe et al., "Genomic structure of the human prototype strain H of hepatitis C virus: Comparison with American and Japanese isolates," *PNAS* 88:10292–10296, 1991.
Takamizawa et al., "Structure and Organization of the Hepatitis C Virus Genome Isolated from Human Carriers," *J. Virology* 65(3):1105–1113, 1991.
Kato et al., "Molecular cloning of the human hepatitis C virus genome from Japanese patients with non–A, non–B hepatitis," *PNAS* 87:9524–9528, 1990.
Ching et al., "Interaction of immune sera with synthetic peptides corresponding to the structural protein region of hepatitis C virus," *PNAS* 89: 3190–3194, 1992.
Inchauspe et al., "Use of Conserved Sequences from Hepatitis C Virus for the Detection of Viral RNA in Infected Sera by Polymerase Chain Reaction," *Hepatology* 14(1): 595–600, 1991.
Kato et al., "A Structural Protein Encoded by the 5' Region of the Hepatitis C Virus Genome Efficiently Detects Viral Infection," *Japanese Journal of Cancer Research* 81(11): 1092–1094, 1990.
Muraiso et al., "A structural protein of hepatitis C virus expressed in E. coli facilitates accurate detection of hepatitis C virus," *Biochem. Biophys. Research Communications* 172(2):511–516, 1990.
Nasoff et al., "Identification of an immunodominant epitope within the capsid protein of hepatitis C virus," *PNAS* 88(12):5462–5466, 1991.
Sallberg et al., "Immunodominant Regions within the Hepatitis C Virus Core and Putative Matrix Proteins," *Journal of Clinical Micro.* 30(8): 1989–1994, 1992.

*Primary Examiner*—Michael P. Woodward
*Assistant Examiner*—Donna C. Wortman
*Attorney, Agent, or Firm*—Seed and Berry LLP

[57] ABSTRACT

The invention relates to a DNA molecule, a polypeptide expressed by the molecule, their use in diagnosis and their methods of production. More particularly, the invention relates to a diagnostic DNA molecule, a diagnostic protein, diagnostic antibodies and protective antigen and antibodies for hepatitis C virus (HCV). The DNA molecule disclosed herein is characterized by the DNA molecule derived from the genome of an HCV, and codes for a polypeptide having the antigenicity of an HCV core antigen protein. The polypeptide may be used in the detection of HCV.

19 Claims, 2 Drawing Sheets

5'-ATGAGCACAAATCCTAAACCTCAAAGAAAAACCAAACGTAACACCAACCGCCGCCCACAG 60
GACGTCAAGTTCCCGGGCGGTGGTCAGATCGTTGGTGGAGTTTACCTGTTGCCGCGCAGG 120
GGCCCCAGGTTGGGTGTGCGCGCGACTAGGAAGACTTCCGAGCGGTCGCAACCTCGTGGA 180
AGGCGACAACCTATCCCCAAGGCTCGCCGGCCCGAGGGCAGGACCTGGGCTCAGCCGGGG 240
TACCCTTGGCCCCTCTATGGCAATGAGGGTCTGGGGTGGGCAGGATGGCTCCTGTCACCC 300
CGAGGCTCTCGGCCTAGTTGGGGCCCCACGGACCCCCGGCGTAGGTCGCGTAATCTGGGT 360
AAGGTCATCGATACCCTCACAGGTGGCTTCGCCGACCTCATGGGGTACATTCCGCTCGTC 420
AGCGCCCCACTAGGAGGCGCTGCCAGGGCCCTGGGCCATGGCGTCCGGGTTCTGGAGGAC 480
GGCGTGAACTATGCAACAGGGAATCTGCCCGGTTGCTCTTTCTCTATCTTCCTCTTAGCT 540
TTGCTGTCTTGTTTGACCATCCCAGCTTCCGCTTACGAGGTGCGCAACGTGTCCGGGATA 600
TACCATGTTACGAACGATTGCTCCAACTCAAGTATCGTGTATGAGGCAGCGGACATGATC 660
ATGCACACC-3' 669

*Fig. 1A*

NH₂-MetSerThrAsnProLysProGlnArgLysThrLysArgAsnThr 15
AsnArgArgProGlnAspValLysPheProGlyGlyGlyGlnIle 30
ValGlyGlyValTyrLeuLeuProArgArgGlyProArgLeuGly 45
ValArgAlaThrArgLysThrSerGluArgSerGlnProArgGly 60
ArgArgGlnProIleProLysAlaArgArgProGluGlyArgThr 75
TrpAlaGlnProGlyTyrProTrpProLeuTyrGlyAsnGluGly 90
LeuGlyTrpAlaGlyTrpLeuLeuSerProArgGlySerArgPro 105
SerTrpGlyProThrAspProArgArgArgSerArgAsnLeuGly 120
LysValIleAspThrLeuThrGlyGlyPheAlaAspLeuMetGly 135
TyrIleProLeuValSerAlaProLeuGlyGlyAlaAlaArgAla 150
LeuGlyHisGlyValArgValLeuGluAspGlyValAsnTyrAla 165
ThrGlyAsnLeuProGlyCysSerPheSerIlePheLeuLeuAla 180
LeuLeuSerCysLeuThrIleProAlaSerAlaTyrGluValArg 195
AsnValSerGlyIleTyrHisValThrAsnAspCysSerAsnSer 210
SerIleValTyrGluAlaAlaAspMetIleMetHisThr-COOH 223

*Fig. 1B*

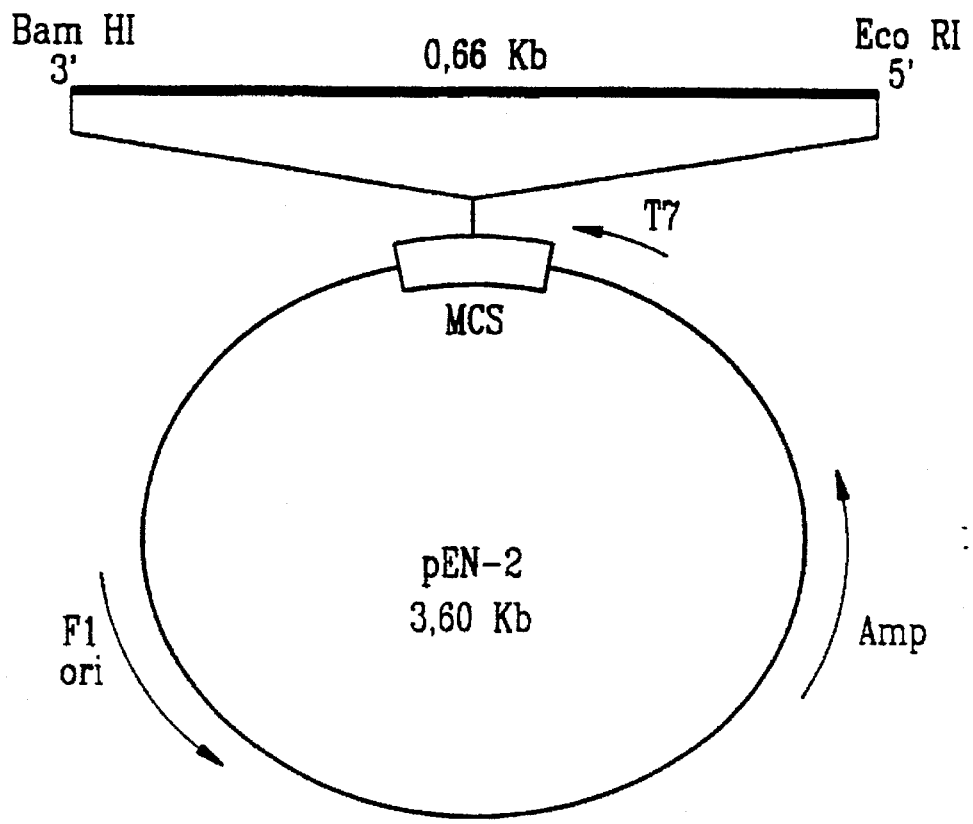
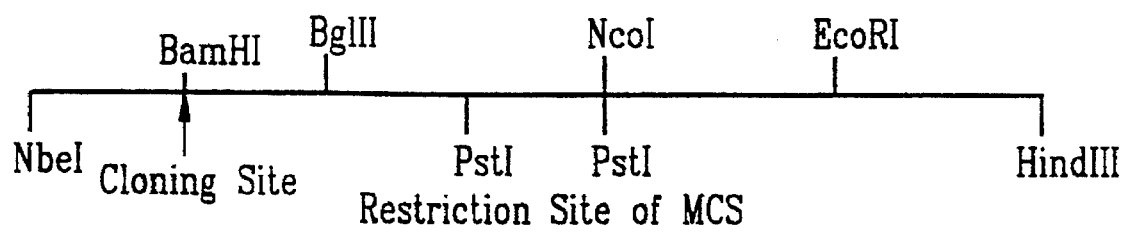
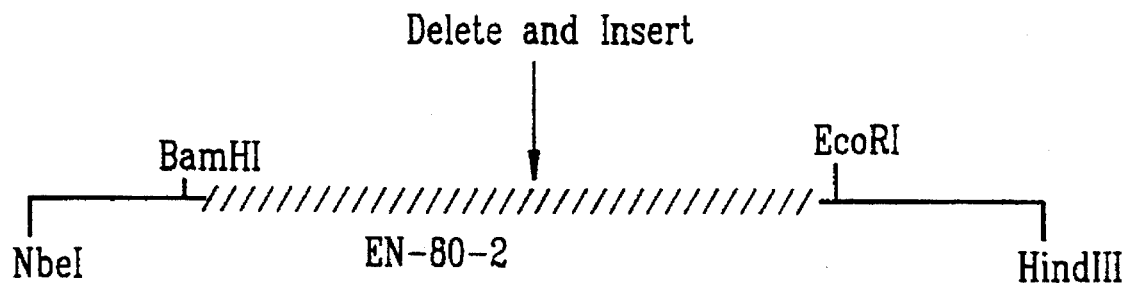
Fig. 2

CORE ANTIGEN PROTEIN OF HEPATITIS C VIRUS, AND DIAGNOSTIC METHOD AND KIT USING THE SAME

CROSS-REFERENCE TO RELATED APPLICATION

This application is a division of U.S. patent application Ser. No. 07/963,483, filed Oct. 16, 1992 now abandoned.

TECHNICAL FIELD OF INVENTION

The invention relates to a DNA molecule, a polypeptide expressed by the molecule, their use in diagnosis and their methods of production. More particularly, the invention relates to a diagnostic DNA molecule, a diagnostic protein, diagnostic antibodies and a protective polypeptide for hepatitis C virus.

BACKGROUND OF THE INVENTION

Most cases of hepatitis arising from blood transfusion are virally-inducted, and distinguishable from other forms of viral-associated liver diseases caused by known hepatitis viruses such as hepatitis A virus (HAY) and hepatitis B virus (HBV). The etiological agent(s) of said Non-A, Non-B hepatitis (NANBH) has long been sought by many research groups and is presently believed to be the hepatitis C virus (HCV). Post-transfusion hepatitis (PTH) occurs in approximately 10% of transfusion patients, and NANBH accounts for up to 90% of these cases. The major problem in this disease is the frequent progression to chronic liver damage (25–55%). Therefore, the demand for sensitive, specific methods for detecting HCV in contaminated blood or blood products is significant.

The hepatitis C virus (HCV) was first identified by molecular cloning and characterization of its RNA genome by Choo, et al. (Science 244: 359-362, 1989). A specific assay using the HCV antigen, designated C100-3, was synthesized using recombinant DNA methods in yeast and detects the antibody of HCV (Science 244: 362-364). A detailed description regarding the genome of HCV, the cDNA sequences derived therefrom, and polypeptides derived from the HCV genome or HCV cDNA as well as methodologies relating to such subject matter, was given in EP 0 318 216 A1 in the name of Chiron Corporation. In particular, the European patent provides a synthesized polypeptide, C100-3, containing 363 viral amino acids which can be used for the detection of HCV antibodies. Now, kits for detecting HCV antibodies on the basis of C100-3 have been commercialized by Abbott Laboratories.

As suggested in the above European patent, HCV may be a flavivirus or flavi-like virus. Generally, with respect to morphology, a flavivirus contains a central nucleocapsid surrounded by a lipid bilayer. It is believed that hepatitis C virus protein is composed of structural proteins including a nucleocapsid (core) protein (C), two glycosylated envelope proteins (E1, E2) and nonstructural proteins (NS1–5). However, the corresponding virus has not yet been isolated nor characterized. It is only confirmed that said C100-3 disclosed by Choo et al. is a protein encoded by part of the nonstructural regions 3–4 of the HCV genome.

Besides, an enzyme-linked immunosorbent assay (ELISA) has also been developed for serological diagnosis of hepatitis C virus (HCV) infection, by using the HCV core protein (p22) synthesized by a recombinant baculovirus by Chiba, et al. (Proc. Natl. Acad. Sci. USA 88:4641–4645, 1991). It was found that C100-3 antibody was not detected in all post-transfusion NANBH cases, probably because of the delayed response to C100-3 antigen. Such delayed response was considered to be due to the fact that the C100-3 is an HCV nonstructural protein. However, Chiba, et al. used an unglycosylated 22-kDa nucleocapsid (core) protein, and established an antibody detection system to develop a specific sensitive method for diagnosing HCV infection.

The invention discloses a DNA molecule coding for an HCV core antigen protein and provides an alternative HCV antibody assay.

SUMMARY OF THE INVENTION

Accordingly, it is an object of the present invention to provide a DNA molecule coding for a polypeptide displaying the antigenicity of a hepatitis C virus (HCV) core antigen protein. More specifically, the invention provides a DNA molecule derived from the genome of HCV. The DNA molecule was cloned from the plasma of a patient with hepatitis C via a Polymerase Chain Reaction (PCR) technique.

Portions of the DNA molecule are useful as probes to diagnose the presence of virus in samples. Additionally, the DNA molecule of the invention is capable of producing, in an appropriate host, viral polypeptides displaying the antigenicity of an HCV core antigen protein.

It is another object of the present invention to provide a polypeptide displaying the antigenicity of an HCV core antigen protein. Said polypeptide was produced by an appropriate host transformed with the DNA molecule of the invention.

Also, it is an object of the present invention to provide a process for producing a polypeptide displaying the antigenicity of an HCV core antigen protein. The process comprises incubating host cells transformed with an expression vector containing a DNA molecule of the invention.

It is still another object of the present invention to provide a method for detecting HCV antibodies in samples by using said HCV core antigen protein as a probe. The method may be carried out by immunoassay or Western blotting which is characterized by using said HCV core antigen as a probe capable of binding to antibodies directed against HCV in samples, to form an antigen-antibody complex.

The invention also includes a method for detecting HCV antibodies in samples by using said HCV core antigen protein combined with an HCV nonstructural protein as a probe.

It is yet another object of the present invention to provide a kit for analyzing samples for the presence of HCV antibodies, the kit, comprising said HCV core antigen protein. Specifically, a kit is useful for an immunoassay for detecting HCV antibodies and comprises said HCV core antigen protein and a suitable solid phase.

It is another further object of the present invention to provide monoclonal and polyclonal antibodies directed against said HCV core antigen protein. Also included in the invention is the process for producing said antibodies by immunizing an animal with said HCV core antigen protein. A method for analyzing HCV in samples can be established by using the obtained antibodies.

It is yet further object of the present invention to provide vaccines for prevention of HCV infection, the vaccines comprising an immunogenic polypeptide of the invention, or an inactivated preparation or an attenuated preparation thereof.

These and other objects, advantages and features of the present invention will be more fully understood and appreciated by reference to the written specification.

BRIEF DESCRIPTION OF THE DRAWINGS

FIG. 1A depicts the nucleotide sequence of the presently claimed invention, which sequence encompasses the entire core region and a part of the envelope region of the hepatitis C virus.

FIG. 1B depicts the amino acid sequence encoded by the nucleotide sequence depicted in FIG. 1A.

FIG. 2 shows the structure of the expression vector pEN-2 constructed by inserting the cDNA coding for an HCV core antigen into a plasmid. The figure also shows a restriction map illustrating the significant features of the vector pEN-2.

DETAILED DESCRIPTION OF THE INVENTION

The present invention provides a DNA molecule coding for a polypeptide displaying the antigenicity of an HCV core antigen protein. The DNA molecule is isolated from nucleic acid sequences present in the plasma of an HCV infected patient which includes the steps of isolating the viral particles from the patient's plasma, extracting and purifying the vital nucleic acid sequences, and then Cloning the desired DNA molecule via a Polymerase Chain Reaction (PCR) technique. The PCR technique comprises of steps of a selection by using specific primers and an amplification by using a reverse transcriptase. The primers used in the PCR are (i) 5'-GGATCCATGAGCACAAATCCTAAACCT-3' (Seq ID No.1) and (ii) 5'-GAATTCGGTGTGCATGATCATGTCCGC-3' (Seq ID No.2)

The cloned DNA molecule is subject to a hybridization with original HCV particles for identification. The molecule thus obtained is designated EN-80-2. The DNA sequence of the molecule EN-80-2 is given in FIG. 1A (Seq ID No.3). The DNA molecule is derived from the genome of the HCV nucleocapsid and envelope regions and has 669 bp.

Portions of the DNA molecule are useful as probes to diagnose the presence of HCV nucleic acids in samples.

The DNA molecule of the present invention is inserted into an appropriate vector to form an expression vector. The vector can be a plasmid, bacteriophage or other DNA sequence which is able to replicate in a host cell. The preferable vector is a plasmid with the promoter lac. Referring to FIG. 2, we have shown an expression plasmid, pEN-2, constructed by a vehicle plasmid and the DNA molecule of the present invention.

An appropriate host is transformed with an expression vector-containing the DNA molecule of the invention and the polypeptide displaying the antigenicity of an HCV core antigen protein can be produced in the transformed host. A process for producing the polypeptide displaying the antigenicity of an HCV core antigen has been established.

The invention also provides a polypeptide displaying the antigenicity of an HCV core antigen protein. The amino acid sequence of the polypeptide is given in FIG. 1B (Seq ID No.4). The polypeptide has a molecular weight of about 25,000 as measured by electrophoresis through a sodium dodecyl sulfate-polyacrylamide gel and is deduced to have about 220 amino acids. The ability of the obtained polypeptide to bind to HCV antibodies is confirmed by Western Blotting. The polypeptide is reactive with the sera of patients with hepatitis C but not reactive with the sera of persons without hepatitis C. This fact suggests that the polypeptide capable of detecting the presence of HCV antibodies in samples holds a potential in diagnosis of hepatitis C. Additionally, the polypeptides displaying the antigenicity of an HCV core antigen, or an inactivated preparation or an attenuated preparation thereof, can be formulated in an immunogenically effective amount as vaccines for prevention of HCV infection.

The method for detecting HCV antibodies in samples is included in the invention. The method is characterized by the HCV core antigen's capability of binding to HCV antibodies as a probe. The method can be carried out by immunoassay or Western Blotting. A preferred method is solid-phase immunoassay. A solid phase, such as microtiter plates, beads and semipermeable membranes, can be used to carry out the immunoassay. Substances useful as a label include enzymes, isotopes, fluorescent materials and any other materials which can be directly detected. The immunoassay is conveniently achieved by a sandwich method, such as an enzyme-linked immunosorbent assay (ELISA). The ELISA comprises: 1) coating the polypeptide of the present invention onto a solid phase, 2) incubating a sample suspected of containing HCV antibodies with the polypeptide coated onto said solid phase under conditions which allow the formation of an antigen-antibody complex, 3) adding an anti-antibody (such as anti-IgG) conjugated with a label to be captured by the resulting antigen-antibody complex bound to the solid phase, and 4) measuring the captured label and determining whether the sample has HCV antibodies.

An alternative assay can be carried out by using the polypeptide of the invention combined with an HCV non-structural protein as a probe. The assay is thought to be more specific and sensitive.

The invention further provides a kit for analyzing samples for the presence of HCV antibodies. The kit comprises a polypeptide of the invention and an appropriate solid phase. Preferably the polypeptide is coated onto the solid phase.

The present invention also provides monoclonal and polyclonal antibodies directed against said HCV core antigen protein. The antibodies are produced by using the polypeptide of the invention as an immunogen through standard procedures for preparing a hybridoma and/or conventional methods. The obtained antibodies are potentially useful for developing a method for detecting HCV.

The following examples are offered to aid in understanding the present invention and are not to be construed as limiting the scope thereof.

EXAMPLES

I. Cloning of an HCV cDNA

The plasma of the patients infected with Hepatitis C virus are collected and ultracentrifuged at 4° C. and then the viral particles are obtained. Subsequently, the viral nucleic acid (RNA) is extracted and purified from the viral particles by using guanidine isothiocyanate and acidic phenol.

The nucleic acid thus obtained is subject to a Polymerase Chain Reaction (PCR). A cDNA molecule is cloned by said PCR wherein the following oligonucleotide sequences are used as primers:

(i) 5'-GGATCCATGAGCACAAATCCTAAACCT-3' (Seq. ID No. 1) and (ii) 5'-GAATTCGGTGTGCATGATCATGTCCGC-3 (Seq. ID No. 2);

and the cloned DNA is amplified by using a reverse transcriptase.

The cloned DNA molecule is subject to a hybridization with original HCV particles for identification. The obtained molecule is designated EN-80-2. The DNA sequence of the molecule EN-80-2 is given in FIG. 1A (Seq ID No.3). The DNA molecule is derived from the genome of HCV nucleocapsid and envelope regions and has 669 bp.

II. Construction of a Plasmid Containing an HCV cDNA

The molecule EN-80-2 is treated with restriction endonucleases Bam HI and EcoRI to obtain a transposon containing said HCV cDNA. The obtained transposon is inserted into a plasmid which is first cleaved with the restriction endonucleases Bam HI and EcoRI, to obtain an expression plasmid, designated pEN-2. The expression of the HCV cDNA is under the control of a promoter lac. The structure of the expression plasmid pEN-2 and a restriction map are given in FIG. 2.

III. Transformation of E. coli

The expression plasmid pEN-2 is incubated with *E. coli* JM109 (DE3) at 37° C. overnight. *E. coli* colonies producing HCV core antigen protein are selected by screening their expression products by Western Blotting.

IV. Production of HCV Core Antigen

The transformed *E. coli* colonies are incubated in a conditioned culture medium. The colonies are centrifuged and lysed by freezing-defrosting cycles and enzyme-digestion. The protein product is released by the lysed cells and purified by chromatography. The purity of the obtained polypeptide is more than 90%.

The polypeptide has a molecular weight of about 25,000 as measured by electrophoresis through a sodium dodecyl sulfate-polyacrylamide gel.

V. Immunological Reactivity of HCV Core Antigen with HCV Antibodies by Western Blotting The purified polypeptide is subject to an SDS PAGE electrophoresis by standard procedures. The SDS-PAGE gel is washed with deionized water at 4° C. for 15 minutes and washed with Blotting Buffer (0.15M sodium phosphate buffer, pH 6.7) at 4° C. for 20 minutes. The peptide map on the gel is then electroblotted onto a nitrocellulose paper under the Blotting Buffer at 1.3 A for 1–1.5 hours. The paper is washed with Wash Buffer (PBS-Tween 20, pH 7.4) and blocked with Blocking Buffer (0.1M NaCl, 5 mM EDTA, 50 mM Tris, pH 7.2–7.4, 0.2% fetal bovine serum albumin, 0.05% Nonidet p-40, 1M urea) overnight.

The paper is reacted with the sera of subjects with/without hepatitis C, which are first diluted with 40% NBBS/Tris-HCl (pH 7.4), 10×, at 40° C. for 2 hours. After the reaction, the paper is washed with Wash Buffer three times. The paper is reacted with an anti-hIgG:HRPO conjugate (which is prepared as described hereafter) at 40° C. for 2 hours. After the reaction, the paper is washed with Wash Buffer three times and then reacted with 10 ml Substrate Solution (0.01% 4-ethloro-1-Napthol, 18% methanol, 0.04M Tris, pH 7.2–7.4, 0.1M NaCl and 0.01% $H_2O_2$) for 20 minutes. The polypeptide of the present invention is reactive with the sera of HCV patients but not reactive with the sera of healthy persons.

VI. ELISA for HCV Antibodies (1) Treatment of Microtiter Plate

The microtiter plate is coated with the purified polypeptide of the invention at appropriate concentrations and blocked with a buffer containing bovine serum albumin. The treated microtiter plate is stored at 2°–8° C.

(2) Preparation of Anti-hIgG:HRPO Conjugate

The purified anti-human Immunoglobulin G (anti-hIgG) is conjugated with horse radish peroxidase (HRPO) using $NaIO_4$ to obtain the anti-IgG:HRPO conjugate. The conjugate is purified by chromatography.

(3) Components of Reagents (a) Wash Solution: Phosphate Buffer containing 0.9% NaCl and Thimerosal.

(b) Anti-hIgG:HRPO Conjugate Solution: the anti-hIgG:HRPO conjugate prepared as described above dissolved in Tris Buffer containing a proteineous stabilizer and antiseptics.

(c) Sample Diluent: Tris Buffer containing a proteineous stabilizer and antiseptics.

(d) OPD Substrate Solution: o-phenylene diamine (OPD) dissolved in citrate-phosphate buffer containing $H_2O_2$. (If the solution becomes orange, it means that the solution has been contaminated and cannot be used any more.)

(e) Stopping Solution: 2N $H_2SO_4$ solution.

(f) Positive/Negative Controls: the serum samples of persons infected with/without hepatitis C diluted with phosphate buffer containing a proteineous stabilizer and antiseptics at an appropriate concentration.

(4) Procedure (a) One hundred and fifty microliter (ul) of test samples diluted with Sample Diluent (1:10) and Positive/Negative Controls are added into the wells of the treated microtiter plate. Some wells have to be retained as substrate blanks.

(b) The plate is gently mixed by shaking and incubated at 37°–40° C. for 1 hour.

(c) The plate is washed with 0.3 ml of Wash Solution per well by a washer three times.

(d) One hundred ul of anti-hIgG:HRPO Conjugate Solution is added to each well.

(e) The plate is incubated by shaking at 37°–40° C. for 30 minutes.

(f) The plate is washed five times.

(g) One hundred ul of OPD Substrate Solution is added into each well and the plate is incubated at 15°–30° C. in the dark for 30 minutes.

(h) One hundred ul of Stopping Solution is added into each well and gently mixed to stop the reaction.

(i) The OD value per well is measured by a spectrophotometer at 492 nm.

(5) Determination

The $OD_{492\ nm}$ value per well subtracts the mean of the readings of the blanks (backgrounds). The difference (PCx-NCx) between the mean of the readings of the positive controls (PCx) and that of the negative controls (NCx) is equal to or more than 0.5.

The Cut-off value (CO) is calculated by the following formula:

$$CO = PCx \times 0.15 + NCx$$

When the readings of test samples are less than the CO value, the samples are considered negative (i.e., HCV antibodies cannot be detected in the samples).

When the readings of test samples are equal to or more than the CO value, the samples are expected to be positive; however, it is necessary to repeat the assay for the samples in duplicate. If the readings of either of the duplicate samples is less than the CO value, the samples are negative. If the duplicate samples are both more than or equal to the cut-off value, the samples will be positive.

When the readings of test samples are more than NCx but less than the CO value by 20%, the samples should be regarded as questionable samples and the assay has to be repeated for those samples.

Twenty-seven samples were tested by the ELISA according to the invention. At the same time, the samples were also tested by the HCV antibody assay by using C100-3 as a probe (i.e., Abbott's kit (II)). The comparison between the test results of Abbott's kit and those of the assay of the invention is given in Table I. It is noted that the results of Sample G 229 was negative by the Abbott's kit (II) but positive by the assay of the present invention. It is suggested that samples infected with HCV cannot be all detected by the Abbott's assay.

TABLE I

| Sample No. | $OD_{492nm}$ | Results | References Abbott's kit (II) |
|---|---|---|---|
| TSGH | 56 | >2.0 | positive | positive |
| TSGH | 57 | >2.0 | positive | positive |
| G | 23 | 1.469 | positive | positive |
| G | 30 | >2.0 | positive | positive |
| G | 32 | >2.0 | positive | positive |
| G | 49 | >2.0 | positive | positive |
| G | 56 | >2.0 | positive | positive |
| G | 58 | >2.0 | positive | positive |
| G | 114 | 1.559 | positive | positive |
| G | 128 | >2.0 | positive | positive |
| G | 186 | >2.0 | positive | positive |
| G | 208 | >2.0 | positive | positive |
| G | 214 | >2.0 | positive | positive |
| G | 231 | >2.0 | positive | positive |
| G | 250 | >2.0 | positive | positive |
| Y | 1 | >2.0 | positive | positive |
| USB | 9 | >2.0 | positive | positive |
| USB | 19 | >2.0 | positive | positive |
| USB | 20 | >2.0 | positive | positive |
| USB | 23 | 0.952 | positive | positive |
| USB | 27 | 0.753 | positive | positive |
| G | 11 | 0.147 | negative | negative |
| G | 12 | 0.077 | negative | negative |
| G | 13 | 0.061 | negative | negative |
| G | 14 | 0.116 | negative | negative |
| G | 15 | 0.139 | negative | negative |
| G | 229 | 0.517 | positive | negative |

VII. Detection of HCV Antibodies by HCV Core Antigen Protein Combined with HCV Nonstructural Protein The method is analogous to the ELISA as described above except that HCV core antigen protein of the invention combined with an HCV nonstructural protein (9:1) is replaced for the HCV core antigen protein to be coated onto the plate.

Twenty-four samples were tested by the above-mentioned method. At the same time, the samples were also tested by Abbott's kit (II). The results are given in Table II. It is suggested that the results of the Abbott's assay is the same of the above-mentioned method.

TABLE II

| Sample No. | $OD_{492nm}$ | Results | References Abbott's kit (II) |
|---|---|---|---|
| TSGH | 56 | >2.0 | positive | positive |
| TSGH | 57 | >2.0 | positive | positive |
| G | 23 | >2.0 | positive | positive |
| G | 26 | >2.0 | positive | positive |
| G | 30 | >2.0 | positive | positive |
| G | 32 | >2.0 | positive | positive |
| G | 49 | >2.0 | positive | positive |
| G | 56 | >2.0 | positive | positive |
| G | 58 | >2.0 | positive | positive |
| G | 114 | >2.0 | positive | positive |
| G | 128 | >2.0 | positive | positive |
| G | 186 | >2.0 | positive | positive |
| G | 214 | >2.0 | positive | positive |
| G | 231 | >2.0 | positive | positive |
| G | 250 | >2.0 | positive | positive |
| Y | 1 | >2.0 | positive | positive |
| USB | 9 | >2.0 | positive | positive |
| USB | 19 | >2.0 | positive | positive |
| USB | 20 | >2.0 | positive | positive |
| USB | 23 | >2.0 | positive | positive |
| USB | 27 | >2.0 | positive | positive |
| G | 92 | 0.038 | negative | negative |
| G | 93 | 0.056 | negative | negative |
| G | 94 | 0.071 | negative | negative |

While only one embodiment of the present invention has been shown and described herein, it will be appreciated that modifications thereof, some of which have been alluded to hereinabove, may still be readily made thereto by those skilled in the art. We, therefore, intend, by the appended claims, to cover the modifications alluded to herein as well as all other modifications which fall within the true spirit and scope of our invention.

We claim:

1. A method for detecting hepatitis C virus (HCV) antibodies in a sample, comprising contacting a partially purified, bacterially-produced core-env polypeptide having the amino acid sequence as given in SEQ ID No: 4, wherein said core-env polypeptide has a molecular weight of about 25,000 daltons and which core-env polypeptide is an hepatitis C virus core antigen polypeptide fused to a part of an envelope region of an hepatitis C virus, with said sample under conditions which allow binding of said polypeptide with antibodies directed against an HCV antigen in said sample to form a antigen-antibody complex, and then detecting said antigen-antibody complex.

2. A method for detecting hepatitis C virus (HCV) antibodies in a sample, comprising contacting a partially purified, bacterially-produced core-env polypeptide which core-env polypeptide is an hepatitis C virus core antigen polypeptide fused to a part of an envelope region polypeptide of an hepatitis C virus wherein said core-env polypeptide is encoded by a nucleic acid molecule that is located between about primer (i) (Seq ID No. 1) and primer (ii) (Seq ID No. 2) and said core-env polypeptide has a molecular weight of about 25,000 daltons with said sample under conditions which allow binding of said polypeptide with antibodies directed against an HCV antigen in said sample to form a antigen-antibody complex, and then detecting said antigen-antibody complex.

3. A method according to claim 1 or 2 which is carried out by solid phase-immunoassay.

4. A method according to claim 3 characterized by using a microtiter plate as said solid phase.

5. A method according to claim 1 or 2 characterized by using an enzyme or isotope substance as a label.

6. A method according to 1 or 2, wherein said contacting further comprises contacting an HCV nonstructural protein antigen with said sample under said conditions.

7. An enzyme-linked immunosorbent assay (ELISA) for detecting hepatitis C virus (HCV) antibodies in samples, which comprises:

1) coating a partially purified, bacterially-produced core-env polypeptide having the amino acid sequence as given in SEQ ID No: 4, wherein said core-env polypeptide has a molecular weight of about 25,000 daltons and which core-env polypeptide is an hepatitis C virus core antigen polypeptide fused to a part of an envelope region of an hepatitis C virus onto a solid phase, 2) contacting a sample suspected of containing HCV antibodies with said polypeptide coated onto the solid phase under conditions which allow the formation of an antigen-antibody complex, 3) adding an anti-human antibody conjugated with an enzyme label to be captured by said antigen-antibody complex bound to the solid phase, and 4) detecting the captured label and determining whether the sample has HCV antibodies.

8. An enzyme-linked immunosorbent assay (ELISA) for detecting hepatitis C virus (HCV) antibodies in samples, which comprises:

1) coating a partially purified, bacterially-produced core-env polypeptide which core-env polypeptide is an hepatitis C virus core antigen polypeptide fused to a part of an envelope region polypeptide of an hepatitis C virus, wherein said core-env polypeptide is encoded by a nucleic acid molecule that is located between about primer (i) (Seq ID No. 1) and primer (ii) (Seq ID No. 2) and said core-env polypeptide has a molecular weight of about 25,000 daltons, onto a solid phase, 2) contacting a sample suspected of containing HCV antibodies with said polypeptide coated onto the solid phase under conditions which allow the formation of an antigen-antibody complex, 3) adding an anti-human antibody conjugated with an enzyme label to be captured by said antigen-antibody complex bound to the solid phase, and 4) detecting the captured label and determining whether the sample has HCV antibodies.

9. An ELISA according to claim 7 or 8 wherein the solid phase is a microtiter plate.

10. An ELISA according to claim 7 or 8 wherein the label is horseradish peroxidase.

11. An ELISA according to claim 7 or 8 wherein said contacting further comprises contacting said sample with an HCV nonstructural protein under conditions which allow the formation of an HCV nonstructural protein-antibody complex.

12. A kit for an enzyme-linked immunosorbent assay (ELISA) for detecting hepatitis C virus (HCV) antibodies in samples, comprising a partially purified, bacterially-produced core-env polypeptide having the amino acid sequence as given in SEQ ID No: 4, wherein said core-env polypeptide has a molecular weight of about 25,000 daltons and which core-env polypeptide is an hepatitis C virus core antigen polypeptide fused to a part of an envelope region of an hepatitis C virus coated on a suitable solid phase, and an anti-human antibody conjugated with an enzyme label.

13. A kit for an enzyme-linked immunosorbent assay (ELISA) for detecting hepatitis C virus (HCV) antibodies in samples, comprising a partially purified, bacterially-produced core-env polypeptide which core-env polypeptide is an hepatitis C virus core antigen polypeptide fused to a part of an envelope region polypeptide of an hepatitis C virus wherein said core-env polypeptide is encoded by a nucleic acid molecule that is located between about primer (i) (Seq ID No. 1) and primer (ii) (Seq ID No. 2) and said core-env polypeptide has a molecular weight of about 25,000 daltons, said core-env polypeptide coated on a suitable solid phase, and an anti-human antibody conjugated with an enzyme label.

14. A kit according to claim 12 or 13, wherein the label is horseradish peroxidase.

15. Antibodies directed against an hepatitis C virus (HCV) core antigen protein which are elicited by immunizing an animal using a partially purified, bacterially-produced core-env polypeptide having the amino acid sequence as given in SEQ ID No: 4, wherein said core-env polypeptide has a molecular weight of about 25,000 daltons and which core-env polypeptide is an hepatitis C virus core antigen polypeptide fused to a part of an envelope region of an hepatitis C virus as an immunogen.

16. Antibodies directed against an hepatitis C virus (HCV) core antigen protein which are elicited by immunizing an animal using a partially purified, bacterially-produced core-env polypeptide which core-env polypeptide is an hepatitis C virus core antigen polypeptide fused to a part of an envelope region polypeptide of an hepatitis C virus wherein said core-env polypeptide is encoded by a nucleic acid molecule that is located between about primer (i) (Seq ID No. 1) and primer (ii) (Seq ID No. 2) and said core-env polypeptide has a molecular weight of about 25,000 daltons as an immunogen.

17. Antibodies according to claim 15 or 16 which are polyclonal antibodies.

18. Antibodies according to claim 15 or 16 which are monoclonal antibodies.

19. A method for analyzing HCV antigen in a sample comprising contacting said antibodies of claim 15 or 16 with said sample under conditions suitable for said antibodies to form a complex with a hepatitis C virus (HCV) antigen protein, and detecting said complex and thereby determining whether HCV antigen is in said sample.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
GGATCCATGA GCACAAATCC TAAACCT                                                    27
```

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (xi) SEQUENCE DESCRIPTION: SEQ ID NO:2:

```
GAATTCGGTG TGCATGATCA TGTCCGC                                                    27
```

(2) INFORMATION FOR SEQ ID NO:3:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..669

(xi) SEQUENCE DESCRIPTION: SEQ ID NO:3:

```
ATG  AGC  ACA  AAT  CCT  AAA  CCT  CAA  AGA  AAA  ACC  AAA  CGT  AAC  ACC  AAC     48
Met  Ser  Thr  Asn  Pro  Lys  Pro  Gln  Arg  Lys  Thr  Lys  Arg  Asn  Thr  Asn
 1              5                   10                  15

CGC  CGC  CCA  CAG  GAC  GTC  AAG  TTC  CCG  GGC  GGT  GGT  CAG  ATC  GTT  GGT     96
Arg  Arg  Pro  Gln  Asp  Val  Lys  Phe  Pro  Gly  Gly  Gly  Gln  Ile  Val  Gly
                 20                   25                  30

GGA  GTT  TAC  CTG  TTG  CCG  CGC  AGG  GGC  CCC  AGG  TTG  GGT  GTG  CGC  GCG    144
Gly  Val  Tyr  Leu  Leu  Pro  Arg  Arg  Gly  Pro  Arg  Leu  Gly  Val  Arg  Ala
             35                  40                  45

ACT  AGG  AAG  ACT  TCC  GAG  CGG  TCG  CAA  CCT  CGT  GGA  AGG  CGA  CAA  CCT    192
Thr  Arg  Lys  Thr  Ser  Glu  Arg  Ser  Gln  Pro  Arg  Gly  Arg  Arg  Gln  Pro
         50                  55                  60

ATC  CCC  AAG  GCT  CGC  CGG  CCC  GAG  GGC  AGG  ACC  TGG  GCT  CAG  CCG  GGG    240
Ile  Pro  Lys  Ala  Arg  Arg  Pro  Glu  Gly  Arg  Thr  Trp  Ala  Gln  Pro  Gly
 65              70                  75                  80

TAC  CCT  TGG  CCC  CTC  TAT  GGC  AAT  GAG  GGT  CTG  GGG  TGG  GCA  GGA  TGG    288
Tyr  Pro  Trp  Pro  Leu  Tyr  Gly  Asn  Glu  Gly  Leu  Gly  Trp  Ala  Gly  Trp
                 85                  90                  95

CTC  CTG  TCA  CCC  CGA  GGC  TCT  CGG  CCT  AGT  TGG  GGC  CCC  ACG  GAC  CCC    336
Leu  Leu  Ser  Pro  Arg  Gly  Ser  Arg  Pro  Ser  Trp  Gly  Pro  Thr  Asp  Pro
            100                 105                 110

CGG  CGT  AGG  TCG  CGT  AAT  CTG  GGT  AAG  GTC  ATC  GAT  ACC  CTC  ACA  GGT    384
Arg  Arg  Arg  Ser  Arg  Asn  Leu  Gly  Lys  Val  Ile  Asp  Thr  Leu  Thr  Gly
        115                 120                 125

GGC  TTC  GCC  GAC  CTC  ATG  GGG  TAC  ATT  CCG  CTC  GTC  AGC  GCC  CCA  CTA    432
Gly  Phe  Ala  Asp  Leu  Met  Gly  Tyr  Ile  Pro  Leu  Val  Ser  Ala  Pro  Leu
    130                 135                 140

GGA  GGC  GCT  GCC  AGG  GCC  CTG  GGC  CAT  GGC  GTC  CGG  GTT  CTG  GAG  GAC    480
Gly  Gly  Ala  Ala  Arg  Ala  Leu  Gly  His  Gly  Val  Arg  Val  Leu  Glu  Asp
145                 150                 155                 160

GGC  GTG  AAC  TAT  GCA  ACA  GGG  AAT  CTG  CCC  GGT  TGC  TCT  TTC  TCT  ATC    528
```

| | | | | | | | | | | | | | | | | |
|---|---|---|---|---|---|---|---|---|---|---|---|---|---|---|---|---|
| Gly | Val | Asn | Tyr | Ala | Thr | Gly | Asn | Leu | Pro | Gly | Cys | Ser | Phe | Ser | Ile | |
| | | | | 165 | | | | | 170 | | | | | 175 | | |
| TTC | CTC | TTA | GCT | TTG | CTG | TCT | TGT | TTG | ACC | ATC | CCA | GCT | TCC | GCT | TAC | 576 |
| Phe | Leu | Leu | Ala | Leu | Leu | Ser | Cys | Leu | Thr | Ile | Pro | Ala | Ser | Ala | Tyr | |
| | | | 180 | | | | | 185 | | | | | 190 | | | |
| GAG | GTG | CGC | AAC | GTG | TCC | GGG | ATA | TAC | CAT | GTT | ACG | AAC | GAT | TGC | TCC | 624 |
| Glu | Val | Arg | Asn | Val | Ser | Gly | Ile | Tyr | His | Val | Thr | Asn | Asp | Cys | Ser | |
| | | 195 | | | | | 200 | | | | | 205 | | | | |
| AAC | TCA | AGT | ATC | GTG | TAT | GAG | GCA | GCG | GAC | ATG | ATC | ATG | CAC | ACC | | 669 |
| Asn | Ser | Ser | Ile | Val | Tyr | Glu | Ala | Ala | Asp | Met | Ile | Met | His | Thr | | |
| | 210 | | | | | 215 | | | | | 220 | | | | | |

( 2 ) INFORMATION FOR SEQ ID NO:4:

( i ) SEQUENCE CHARACTERISTICS:
        ( A ) LENGTH: 223 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ser | Thr | Asn | Pro | Lys | Pro | Gln | Arg | Lys | Thr | Lys | Arg | Asn | Thr | Asn |
| 1 | | | | 5 | | | | | 10 | | | | | 15 | |
| Arg | Arg | Pro | Gln | Asp | Val | Lys | Phe | Pro | Gly | Gly | Gly | Gln | Ile | Val | Gly |
| | | | 20 | | | | | 25 | | | | | 30 | | |
| Gly | Val | Tyr | Leu | Leu | Pro | Arg | Arg | Gly | Pro | Arg | Leu | Gly | Val | Arg | Ala |
| | | 35 | | | | | 40 | | | | | 45 | | | |
| Thr | Arg | Lys | Thr | Ser | Glu | Arg | Ser | Gln | Pro | Arg | Gly | Arg | Arg | Gln | Pro |
| | 50 | | | | | 55 | | | | | 60 | | | | |
| Ile | Pro | Lys | Ala | Arg | Arg | Pro | Glu | Gly | Arg | Thr | Trp | Ala | Gln | Pro | Gly |
| 65 | | | | | 70 | | | | | 75 | | | | | 80 |
| Tyr | Pro | Trp | Pro | Leu | Tyr | Gly | Asn | Glu | Gly | Leu | Gly | Trp | Ala | Gly | Trp |
| | | | | 85 | | | | | 90 | | | | | 95 | |
| Leu | Leu | Ser | Pro | Arg | Gly | Ser | Arg | Pro | Ser | Trp | Gly | Pro | Thr | Asp | Pro |
| | | | 100 | | | | | 105 | | | | | 110 | | |
| Arg | Arg | Arg | Ser | Arg | Asn | Leu | Gly | Lys | Val | Ile | Asp | Thr | Leu | Thr | Gly |
| | | 115 | | | | | 120 | | | | | 125 | | | |
| Gly | Phe | Ala | Asp | Leu | Met | Gly | Tyr | Ile | Pro | Leu | Val | Ser | Ala | Pro | Leu |
| | 130 | | | | | 135 | | | | | 140 | | | | |
| Gly | Gly | Ala | Ala | Arg | Ala | Leu | Gly | His | Gly | Val | Arg | Val | Leu | Glu | Asp |
| 145 | | | | | 150 | | | | | 155 | | | | | 160 |
| Gly | Val | Asn | Tyr | Ala | Thr | Gly | Asn | Leu | Pro | Gly | Cys | Ser | Phe | Ser | Ile |
| | | | | 165 | | | | | 170 | | | | | 175 | |
| Phe | Leu | Leu | Ala | Leu | Leu | Ser | Cys | Leu | Thr | Ile | Pro | Ala | Ser | Ala | Tyr |
| | | | 180 | | | | | 185 | | | | | 190 | | |
| Glu | Val | Arg | Asn | Val | Ser | Gly | Ile | Tyr | His | Val | Thr | Asn | Asp | Cys | Ser |
| | | 195 | | | | | 200 | | | | | 205 | | | |
| Asn | Ser | Ser | Ile | Val | Tyr | Glu | Ala | Ala | Asp | Met | Ile | Met | His | Thr | |
| | 210 | | | | | 215 | | | | | 220 | | | | |